(12) United States Patent
Carson

(10) Patent No.: US 8,877,218 B2
(45) Date of Patent: Nov. 4, 2014

(54) TWO COMPONENT INTERACTIVE EMULSION PRODUCT

(75) Inventor: John C. Carson, Union City, NJ (US)

(73) Assignee: Carson Product Development, Inc., Union City, NJ (US)

( * ) Notice: Subject to any disclaimer, the term of this patent is extended or adjusted under 35 U.S.C. 154(b) by 0 days.

(21) Appl. No.: 13/276,445

(22) Filed: Oct. 19, 2011

(65) Prior Publication Data

US 2012/0058062 A1 Mar. 8, 2012

Related U.S. Application Data

(63) Continuation-in-part of application No. PCT/US2010/031707, filed on Apr. 20, 2010.

(60) Provisional application No. 61/214,211, filed on Apr. 21, 2009.

(51) Int. Cl.

| | | |
|---|---|---|
| *A61K 8/00* | (2006.01) | |
| *A61K 8/02* | (2006.01) | |
| *A61K 8/55* | (2006.01) | |
| *A61K 8/41* | (2006.01) | |
| *A61K 8/06* | (2006.01) | |
| *A61K 31/185* | (2006.01) | |
| *A61K 8/36* | (2006.01) | |
| *A61Q 19/00* | (2006.01) | |
| *A61Q 17/04* | (2006.01) | |

(52) U.S. Cl.
CPC ............... *A61K 31/185* (2013.01); *A61K 8/55* (2013.01); *A61Q 17/04* (2013.01); *A61K 2800/88* (2013.01); *A61K 8/416* (2013.01); *A61K 2800/882* (2013.01); *A61K 8/06* (2013.01); *A61K 8/556* (2013.01); *A61K 8/361* (2013.01); *A61Q 19/00* (2013.01)

USPC ......................................... 424/401; 424/70.19

(58) Field of Classification Search
None
See application file for complete search history.

(56) References Cited

U.S. PATENT DOCUMENTS

| | | | |
|---|---|---|---|
| 5,020,694 A | | 6/1991 | Pettengill |
| 5,289,949 A | | 3/1994 | Gentile |
| 5,589,177 A | * | 12/1996 | Herb et al. ............... 424/401 |
| 5,645,193 A | | 7/1997 | Gentile et al. |
| 6,117,436 A | * | 9/2000 | Flemming et al. ........ 424/401 |
| H2013 H | * | 2/2002 | Boyd et al. ............... 424/401 |

FOREIGN PATENT DOCUMENTS

EP 1493429 A1 * 1/2005

* cited by examiner

*Primary Examiner* — Susan Tran
(74) *Attorney, Agent, or Firm* — Henry D. Coleman; R. Neil Sudol

(57) ABSTRACT

The present invention describes, in one aspect, the use of two oppositely charged surfactants as the primary emulsifiers in two separated parts of a product. The emulsifiers are chosen such that when the two parts of the emulsion product are mixed, the emulsifiers react to form water insoluble compounds that are no longer able to function as emulsifiers, thus, the oil phase of the emulsion is precipitated onto the skin along with the emulsifier reaction product. Since none of the deposited materials are water soluble, or capable of functioning as emulsifiers, the deposited oil phase is extremely resistant to being washed off. This technology finds applications in hand and body creams and lotions, baby care products, sunscreens, skin protective products, makeup systems, and automotive and furniture polishes.

23 Claims, No Drawings

TWO COMPONENT INTERACTIVE EMULSION PRODUCT

RELATED APPLICATIONS/CLAIM OF PRIORITY

This application is a continuation-in-part application of PCT/US2010/31707, filed 20 Apr. 2010 entitled "Two Component Interactive Emulsion Product", which claims the benefit of priority of provisional application U.S. 61/214,211 of identical title, filed Apr. 21, 2009, the entire contents of which applications are incorporated by reference herein.

FIELD OF THE INVENTION

This invention relates to the area of emulsion technology with specific applications in cosmetics and toiletries. Further applications may be found in the areas of hard surface polishes and cleansers.

BACKGROUND OF THE INVENTION AND DESCRIPTION OF THE PRIOR ART

A major difficulty for cosmetic emulsions (and for hard surface waxes and polishes) is the fact that the emulsifier is deposited on the surface along with the oil (or wax) phase when an emulsion product is applied. This results in the oil (or wax) phase being readily re-solubilized or emulsified back into water by the deposited emulsifier when the surface is wetted. Thus, the benefits achieved by applying the emulsion product in the first place, can be greatly diminished by rewetting. For example, sunscreen actives can be readily washed off by bathing following the application of a sunscreen lotion. In order to minimize this effect, in the past, many sunscreen lotions were formulated as water-in-oil (w/o) emulsions. These types of emulsions are made with emulsifiers such as cholesterol, lanolin, lanolin alcohol, low HLB emulsifiers and calcium or magnesium fatty acid soaps. These materials are poorly water soluble and, when deposited on skin as part of an emulsion, they have very little ability to re-emulsify the oil phase when the skin is wetted. These formulations, however, tend to feel oily or greasy upon application and often do not dry (or rub-in) to a cosmetically acceptable non-oily film. In addition, they can be fairly difficult to formulate and making a stable w/o lotion or a low viscosity w/o emulsion can be quite a challenge.

In addition to w/o emulsions, polymeric emulsifiers that make oil-in-water (o/w) emulsions are often used to reduce the ability of the oil phase material to re-emulsify. The commonly used polymeric surfactants precipitate (or "plate out" as it is termed) on the skin. This deposition onto the skin is sufficient to reduce the ability of the polymeric surfactant to re-dissolve in water. Further, most of these polymeric surfactants have low surface activity and do not promote the rewetting of the deposited oil phase material by applied water. This combination of effects is used to produce cosmetically acceptable creams and lotions that have a reduced tendency to wash off. Such formulations find use in water resistant or water proof sunscreen products.

While the use of polymeric surfactants can produce cosmetically acceptable products with very good water resistance, the feel of these products is not always desirable because, upon application, the polymers can feel slimy and the emulsion can take too long to "rub-in". Therefore, the application feel of emulsions made with polymeric surfactants is often very different from that of a conventional soap based o/w emulsion which is the usual type of rub-in feel that is expected by consumers.

SUMMARY AND OBJECTS OF THE INVENTION

In one aspect, the present invention is directed to compositions adapted for delivery onto keratinous tissue of a finished product emulsion in two parts, comprising a first emulsion composition comprising an oil, water and at least one surfactant and a second emulsion composition comprising an oil, water and an least one surfactant wherein when the two parts are mixed and applied to a keratinous surface, wherein a majority by weight of the surfactants (i.e., at least about 50% by weight or more) in said first and second emulsion compositions precipitate out of the emulsion onto the keratinous surface, leaving behind a water-resistant film surface composition.

In preferred aspects of the present invention, in the present composition, the first emulsion composition comprises at least one cationic surfactant and the second emulsion comprises at least one anionic surfactant, wherein the surfactants precipitate out of the emulsion compositions when the first and second emulsion composition are mixed. In alternative aspects of the invention, one of the emulsions may comprise a non-ionic surfactant and in this instance there will be an additional component of the emulsion that will ionically react (i.e., a secondary emulsifier or surfactant or other charged cosmetically acceptable compound or composition, such as a charged polymer) and precipitate with the emulsifier of the second emulsion. In still other alternative aspects of the invention, one or both of the emulsions may further include a non-ionic surfactant (i.e., the non-ionic surfactant is added to the cationic or anionic surfactant in the emulsion). Various further aspects of the composition aspect of the present invention are described in greater detail herein.

In alternative aspects of the invention, methods comprise applying a two-part composition as otherwise disclosed herein onto the keratinous tissue of a subject and combining the two part emulsion product at the point of application, such that the emulsifiers contained in the compositions react ionically and precipitate out of the composition, leaving behind a wash off resistant film or coating on said keratinous tissue.

In certain preferred aspects of the invention, the anionic emulsifier is a fatty acid soap, an alkyl sulfate, an alkyl phosphate or a polymeric anionic emulsifier. In alternative preferred aspects, the cationic emulsifier is a mono fatty quaternary ammonium salt, a di fatty quaternary ammonium salt, a tri fatty quaternary ammonium salt or a polymeric cationic emulsifier.

In other aspects of the invention, the anionic emulsion and the cationic emulsion of the present compositions are co-dispensed from a single package with dual chambers that keep the two emulsions separate before dispensing. The two emulsions can be dispensed as two separate products on the application surface and subsequently mixed by any method, preferably simply by hand. Alternatively, the two emulsions may be combined as they are dispensed from their separate chambers by forcing them through a static mixer or simply combining them in a mixing chamber prior to being dispensed onto the application surface.

In still other aspects of the invention, one or both of the emulsion compositions contain at least one component selected from the group consisting of sunscreen agents, pharmaceutical active ingredients (bioactive agents), pigments, light diffusing materials, colorants, preservatives (such as antimicrobial agents, among others), antioxidants, chelating agents, UV colorant protectants, humectants, polishing agents (such as silicas, clays and rouges), shining agents (such as dimethylpolysiloxanes) and mixtures thereof, among others.

Another aspect of the invention is directed to a composition in two parts, a first emulsion composition comprising an oil, water, at least one surfactant and at least one ionic polymer (i.e., a charged polymer which may be cationic, ionic or zwitterionic, which is cosmetically compatible and, in certain embodiments, has surfactant (emulsifying) characteristics) and a second emulsion composition comprising an oil, water, at least one surfactant and at least one ionic polymer (cationic, anionic or zwitterionic, is cosmetically compatible and, in certain embodiments, has surfactant (emulsifying) characteristics) wherein when said two parts are mixed and applied to a keratinous surface, a majority by weight of the surfactants and a majority by weight of the ionic polymers in said first and second emulsion compositions precipitate out of the emulsion onto the keratinous surface, leaving behind a water-resistant film surface composition. In certain embodiments of this composition, the ionic polymer in the first emulsion is cationic and the ionic polymer in the second emulsion composition is anionic. In still other aspects of this invention, the surfactant in the first emulsion composition is a cationic surfactant and in other embodiments, the surfactant in the second emulsion composition is an anionic surfactant. In still other aspects of this invention, the cationic polymer and/or the anionic polymer is a surfactant. In other aspects of the invention, one or both of the surfactants in the first and second emulsions are nonionic and each of the emulsions contain either an anionic or a cationic polymer such that they are maintained separately until dispensed and mixed.

The present invention addresses a number of concerns in the art by creating two separate emulsions—one formed from anionic surfactants and one from cationic emulsifiers—and combining them immediately prior to or during application, wherein the surfactants precipitate out leaving behind a wash off resistant film on the surface (keratinous) to which the two part composition is applied. The combination causes the anionic and cationic emulsifiers to react to form a large molecular weight, wax-like, water insoluble neutral salt that is incapable of forming an emulsion. The two emulsifiers are therefore effectively removed as functional components allowing the oil phase to deposit on the skin. Since the emulsifiers are non-functional in this combined state, and have no surface activity, they cannot assist in the wetting of the deposited oil phase and they do not assist in re-emulsification of the deposited oils from the skin. Further, the combined emulsifier neutral salt can function as a "water proofing" agent itself (since it is insoluble in water once precipitated) and it can contribute to the aesthetic feel of the combined cream or lotion since it is now essentially a high molecular weight "ionic wax".

It is an object of this invention to provide two separate oil-in-water emulsion products—one made with anionic emulsifiers and the second made with cationic emulsifiers—such that, when they are combined at the point of use, the emulsifiers react becoming nonfunctional as emulsifiers and release their internal oil phases.

It is an object of this invention to provide two separate oil-in-water emulsion products—one made with anionic emulsifiers and the second made with cationic emulsifiers—such that, when they are combined at the point of use, the emulsifiers react becoming nonfunctional as surfactants and therefore do not promote the rewetting and removal or re-emulsification of the deposited oil phases.

It is also an object of this invention that either the anionic or cationic or both of the emulsifiers may be traditional monomeric emulsifiers or one or both of them may be polymeric.

It is yet another object of this invention that either the anionic or cationic emulsions or both emulsions may contain more than one emulsifier and these emulsifiers do not have to be of the same ionic type (for example they may be nonionic).

Still a further object of this invention that both or only one of the emulsions may contain materials in addition to the required anionic or cationic emulsifiers that are used to effect the formula's stability, preservation, color, odor, viscosity, rheology, application, feel, function on skin and the delivery of active materials (such as sunscreens) and medicaments.

It is an additional object of this invention that the two emulsions may be dispensed from separate packages with subsequent mixing either prior to or during application.

It is an object of this invention that the two emulsions may be co-dispensed form a single package and subsequently mixed either prior to or during application.

It is an object of this invention that the two emulsions may be co-dispensed through a mixing devise prior to application.

It is an object of this invention that the two emulsions may be co-dispensed through an aerosol, pressurized or manual pump dispenser.

It is an object of this invention that one or both of the two emulsions may contain solid materials such as pigments or colorants for use as a cosmetic make-up or mascara.

It is an object of this invention that one or both of the two emulsions may contain waxes and/or other shine and appearance enhancing ingredients (such as polydimethylsiloxanes) for use as a wax or polish for hard surfaces.

It is an object of this invention that one or both of the two emulsions may contain abrasive materials and/or solvents and appearance enhancing ingredients for use as a polishing and cleansing medium for hard surfaces.

Any one or more of these and/or other objects of the present invention may be readily gleaned from the description of the invention which is presented herein.

DETAILED DESCRIPTION OF THE INVENTION

Pursuant to the present invention, a composition, preferably a personal care composition, is prepared in two parts comprising an emulsion in each of said two parts, the first part comprising a first surfactant (which may comprise one or more surfactants) and the second part comprising a second surfactant (which may comprise one or more surfactants), such that the two parts of the composition, when mixed (for example, prior to use, or upon application to keratinous tissue of a subject), the surfactants substantially (a majority by weight of the surfactants in the two emulsion compositions) precipitate out of the mixed emulsion (at least about 50%, about 60%, about 70%, about 75%, about 80%, about 90%, about 95%, about 98%, about 99%, about 99.5% or nearly 100% by weight of the two surfactants precipitate out) onto the skin or other keratinous tissue of the subject to which the personal care composition is applied, leaving behind a composition on the surface of the keratinous tissue which has substantially reduced surfactant efficacy and a film which resists moisture and removal by aqueous solutions.

In preferred aspects of the invention, the first emulsion comprises one or more cationic or anionic surfactant (generally, if more than one surfactant, of the same or neutral charge) and the second emulsion comprises an anionic or cationic surfactant (generally, if more than one surfactant, of the same or neutral charge) such that, the two surfactants are of opposite ionic charge and when the two emulsions are combined, the surfactants interact with each other and substantially precipitate out of the combined emulsion formulations. In the present invention, generally, a cationic surfactant will interact with an anionic surfactant and precipitate out. In other aspects, a non-ionic surfactant may be used in one or both of the emulsions, with the intent being to affect the precipitation of the surfactants, to change the aesthetics of the individual or combined emulsions and to modify the combined product wash off resistance.

In certain preferred aspects of the invention, the (total) molar ratio of the surfactant(s) in the first emulsion that will be available to react with the surfactant in the second emulsion is preferably in the range of from about 0.5 to about 1 and from about 1 to about 2 of the molar ratio of the surfactant(s) in the second emulsion and varies according to the amount of surfactant which is desirably precipitated when the two emulsion compositions are combined.

Preferably, the present invention is provided in two emulsion composition parts which are packaged separately in such a manner that they can be co-dispensed and either mixed immediately before being applied to a surface or they can be co-dispensed and mixed as they are being applied to the surface (generally, a keratinous tissue surface—skin, nails, hair—other tissue surfaces). Formulas that are acceptable for aesthetics, physical stability and contain either anionic and cationic emulsifiers are well known in the personal care industry.

The following definitions are used to describe the present invention. In instances where a term is or is not specifically defined, the most common meaning of the term when used in the present invention by those of ordinary skill will apply.

The term "patient" or "subject" is used to describe an individual (i.e., an animal, especially including a mammal, such as a human) to whom the compositions according to the present invention are applied.

The term "surface" shall mean a biological surface, especially including a keratinous surface such as skin, hair and ungual tissue on a subject.

The term "effective" is used throughout the specification to describe components which are included in the compositions according to the present invention in amounts which effect an intended result. All components which are included in compositions according to the present invention are included in effective amounts. In the case of surfactants, these compounds or compositions are included in amounts effective to produce an emulsion composition, which, when combined with other emulsion compositions as otherwise described herein on a surface (preferably, a keratinous surface), precipitate out of solution, preferably leaving behind a water-resistant film in place on the surface to which the compositions have been applied.

The term "emulsion", "oil-in-water (o/w) emulsion" and "water-in-oil (w/o) emulsion" are used throughout the specification to describe compositions according to the present invention. An "emulsion" according to the present invention is a cosmetically acceptable cream or lotion which is generally formed by the suspension of a very finely divided liquid, in the case of a w/o emulsion it would be water, dispersed in another liquid, in this case, an oil. Alternatively, an oil may be dispersed in water to form an o/w emulsion. In the present invention, o/w emulsions are preferred, and perforce must be formed from two oppositely charged surfactant(s) or emulsifying systems that are separated until intentionally combined at the point of use. The term emulsion is used to distinguish the present compositions from compositions which contain at least two distinct physically separated phases, i.e., an oil phase and a water phase.

The anionic emulsions are made with (medium to) high HLB (about 8.5 to about 20 and higher on the HLB scale), fatty, anionic surfactants such as, but not limited to: soaps (most preferably stearic acid or behenic acid soaps), alkyl phosphates, alkyl sulfates, alkyl sarcosinates, alkyl taurates, alkyl ether sulfates and alkyl ethoxy carboxylates. The defining characteristics are that the surfactant have at least one alkyl group of about 14 to about 36 carbons (including linear, branch-chained and cyclic alkyl groups) and at least one water soluble ionizable anionic group.

The cationic emulsions are made with (medium to) high HLB, fatty, cationic surfactants such as, but not limited to: alkyl trimethyl ammonium chlorides, alkyl trimethyl ammonium methosulfates, alkyl dimethyl ethyl ammonium ethosulfates, alkyl dimethyl benzyl ammonium chlorides, dialkyl dimethyl ammonium chlorides, dialkyl dimethyl ammonium methosulfates, dialkyl methylethyl ammonium ethosulfates, trialkyl methyl ammonium chloride, trialkyl methyl ammonium methosulfate, trialkyl ethyl ammonium ethosulfate, steapyrium chloride, lapyrium chloride, alkyl imidazolines and the like. The defining characteristics are that the surfactant have at least one alkyl group of about 14 to about 36 carbons and at least one water soluble ionizable cationic group.

The cationic emulsions may also be made with fatty alkyl amine salts such as, but not limited to: fatty alkyl primary amines acidified with acetic, lactic, glycolic, citric, malic, maleic, tartaric, fumaric and/or mineral acids; and/or fatty alkyl methyl amines, fatty alkyl ethyl amines, fatty alkyl monoalkanol amines, fatty alkyl propyl amines, fatty alkyl dimethyl amines, fatty alkyl diethyl amines, fatty alkyl dipropyl amines, fatty alkyl dialkanol amines, fatty alkyl ethoxylated amines, difatty alkyl methyl amine, difatty alkyl ethyl amines, difatty alkyl alkanol amines; and/or fatty amidopropyl dimethylamines, fatty amidoethyl dimethylamines, fatty amido morpholine acidified with acetic, lactic, glycolic, citric, malic, maleic, tartaric, fumaric and/or mineral acids.

The high HLB surfactants (i.e., with HLB values from about 8.5 and above) described above (whether anionic or cationic) may be used singly to form an emulsion, but they are most often used in combination with low HLB nonionic surfactants (so called: low HLB secondary surfactants—with HLB values from about 0 to about 8) to form the emulsion and to make additional emulsion stabilizing material. Examples of suitable low HLB surfactants are, but not limited to: fatty alcohols such as stearyl alcohol, cetyl alcohol, fatty mono glycerides such as glyceryl monostearate, fatty acid esters of polyhydric alcohols such as propylene glycol monostearate, sorbitan monostearate, ethylene glycol monstearate, sucrosedistearate, fatty acid alkanolamides and the like having fatty groups comprising about 14 to about 36 carbons and being saturated, unsaturated, straight chained or branched. The defining characteristics of these secondary surfactants are that they have at least one alkyl group composed of from about 14 to about 36 carbons and at least one water soluble nonionic group and an HLB in the range of from 0 to about 8.

In addition, the anionic surfactant (emulsifier) may be a polymer. For example, alkyl acrylate copolymers, such as acrylates C10-30 Alkyl Acrylate Crosspolymer (INCI name) are particularly useful as emulsifiers and viscosity controlling agents. These polymeric anionic emulsifiers may be used alone or in combination with other anionic surfactants and/or with low HLB secondary surfactants.

In addition, the cationic emulsifier may be a polymer. Cationic polyurethanes such as Di-PEG-2 Soyamine IPDI (INCI name), Di-PEG-15 Soyamine IPDI (INCI name), the quaternized salts of Di-PEG-2 Soyamine IPDI, Polyquaternium 60 and it's behenyl analog (Polylipid B available from Alzo International, Inc., Sayreville, N.J. USA) are particularly useful as emulsifiers and viscosity controlling agents. Also, fatty, quaternized ethoxylated cellulose may be used. These polymeric cationic emulsifiers may be used alone and/or in combination with other cationic surfactants or with low HLB secondary surfactants.

Exemplary anionic emulsifiers for use in the present invention include, for example, soaps, especially the sodium, potassium and triethanolammonium salts of myristic, palmitic, stearic, oleic, isostearic, isooctyldodecanoic, erucic and behenic acids; sulfuric acid esters of fatty alcohols, e.g. sodium lauryl sulfate, sodium cetyl sulfate, high fatty acid esters of low molecular weight alkylol sulfonic acids, e.g., the oleic acid or stearic acid ester of isethionic acid, sulfated higher fatty acid alkanolamides such as ethanol amide sulfates, higher fatty acid amides of amine alkyl sulfonic acids, such as lauric amide of taurine, among others and aromatic group containing anionic synthetic emulsifiers, such as sodium dodecyl benzene sulfonate. Additional exemplary anionic surfactants also include phosphate esters, such as TEA Cetyl Phosphate (Amphisol) and Crodafos CES (a mixture of cetearyl alcohol, dicetyl phosphate and ceteth-10 phosphate).

Exemplary cationic surfactants include ammonium and quaternary salts of fatty amines and substituted fatty amines, among others. Stearyl dimethyl benzyl ammonium chloride, stearamidopropyl dimethyl ethyl ammonium ethosulfate distearyl dimethyl ammonium chloride (Quaternium 18), behenyl trimethyl ammonium chloride, behenyl trimethyl ammonium methosulfate, behenamidopropyl dimethyl ethyl ammonium ethosulfate, behenamidopropyl trimethyl ammonium chloride, behenamidopropyl trimethyl ammonium methosulfate, Ceraphyl 70 (Quaternium 70) and the like are especially preferred. Ammonium salts such as stearamidopropyl dimethyl ammonium salts, behenamidopropyl dimethyl ammonium salts, isostearamidopropyl morpholine salts, stearyl dimethyl ammonium salts and behenyl dimethyl ammonium salts made by neutralizing the amine with citric, lactic, glycolic, fumaric, tartaric, malic or any mineral acid are also preferred.

The preferred anionic polymeric surfactants are the crosslinked copolymers of acrylic acid and $C_{10-30}$ alkyl acrylates (e.g., the Pemulens from Noveon/Lubrizol). In addition to these anionic polymeric surfactants, preferred anionic polymers used to improve deposition and film formation are the Carbomers, i.e., crosslinked carboxy vinyl polymers of acrylic acid, polycarboxylates, e.g., Gantrez polymers from ISP, other acrylate polymers, polystyrene sulfonates and sodium carboxymethyl celluloses The preferred cationic polymeric surfactants are the polyurethane amine and polyurethane quaternized ammonium polymers from Alzo International, Inc. sold under the Polyderm and Polylipid brand names. Further examples of a useful cationic polymeric surfactants are the Crodacel (Croda, Inc.) and Quatrisoft (Dow Chemical) quaternized cellulosic polymers. In addition to the cationic polymeric surfactants, preferred cationic polymers used to improve deposition and film formation are Polyquaternium 10, Guar Hydroxypropyltrimonium Chloride, the Merquat polymers from Nalco, polyethylene imine, polyacrylamidopropyl-trimonium chloride, polymethacrylamidopropyltrimonium chloride, Dermacryl and Celquat.

In the present invention while it is noted that an emulsion containing an effective amount of a cationic surfactant may be combined with an emulsion containing an effective amount of an anionic surfactant on a keratinous surface to produce a precipitated surfactant combination certain combinations of cationic and anionic surfactants are preferred for use in the present invention. In particular, certain preferred combinations of anionic and cationic surfactants include higher molecular weight materials such as the behenic and stearic derivatives for both the anionic and cationic moieties. However, the precipitated combination may have a less than aesthetic feel, may not form a smooth film or may not combine readily with other formula ingredients, thus requiring some emulsion and deposition modifying ingredients. These may take the form of the lower molecular weight surfactants, polymers and polymeric surfactants described. In addition, while the preferred reaction for the polymeric surfactants may be a combination of Pemulen with Polylipid B because this combination produces a very water resistant film and barrier upon precipitation, the reaction can be modified to affect the application and feel by the addition of other anionic and cationic surfactants as described. Finally, the feel and deposition of the anionic and cationic surfactant reaction product can be modified by adding oily materials, other polymers, solvents such as cosmetic glycols and/or nonionic surfactants.

The term "oil" is used throughout the specification to describe any of various lubricious, hydrophobic and combustible substances obtained from animal, vegetable and mineral matter. Oils for use in the present invention may include petroleum-based oil derivatives such as purified petrolatum and mineral oil. Petroleum-derived oils include aliphatic or wax-based oils, aromatic or asphalt-based oils and mixed base oils and may include relatively polar and non-polar oils. "Non-polar" oils are generally oils such as petrolatum or mineral oil or its derivatives which are hydrocarbons and are more hydrophobic and lipophilic compared to synthetic oils, such as esters, which may be referred to as "polar" oils. It is understood that within the class of oils, that the use of the terms "non-polar" and "polar" are relative within this very hydrophobic and lipophilic class, and all of the oils tend to be much more hydrophobic and lipophilic than the water phase which is used in the present invention.

Petrolatum (mineral fat, petroleum jelly or mineral jelly) and mineral oil products for use in the present invention may be obtained from a variety of suppliers. These products may range widely in viscosity and other physical and chemical characteristics such as molecular weight and purity. Preferred petrolatum and mineral oil for use in the present invention are those which exhibit significant utility in cosmetic and pharmaceutical products. Cosmetic grade oils are preferred oils for use in the present invention.

Additional oils for use in the present invention may include, for example, mono-, di- and tri-glycerides which may be natural or synthetic (derived from esterification of glycerol and at least one organic acid, saturated or unsaturated, such as for example, such as butyric, caproic, palmitic, stearic, oleic, linoleic or linolenic acids, among numerous others, preferably a fatty organic acid, comprising between 8 and 26 carbon atoms). Glyceride esters for use in the present invention include vegetable oils derived chiefly from seeds or nuts and include drying oils, for example, linseed, iticica and tung, among others; semi-drying oils, for example, soybean, sunflower, safflower and cottonseed oil; non-drying oils, for example castor and coconut oil; and other oils, such as those used in soap, for example palm oil. Hydrogenated vegetable oils also may be used in the present invention. Animal oils are also contemplated for use as glyceride esters and include, for example, fats such as tallow, lard and stearin and liquid fats, such as fish oils, fish-liver oils and other animal oils, including sperm oil, among numerous others.

In addition, a number of other "oils" may be used, including $C_{12}$ to $C_{30}$ (or higher) fatty esters (other than the glyceride esters, which are described above) or any other acceptable cosmetic ester or emollient such as, but not limited to jojoba oil, isopropyl myristate, isopropyl palmitate, 2-ethylhexyl-2-ethylhexanoate, 2-ethylhexylisononanoate, isononyl-isononanoate, di2-ethylhexyladipate, diisopropyladipate, glyceryl tricaprylate/caprate, pentaerythrityl tetracaprate/caprylate, pentaerythrityl tetraisostearate, diglyceryl diisostearate, and the like.

In addition to the above-described oils, certain essential oils derived from plants such as volatile liquids derived from flowers, stems and leaves and other parts of the plant which may include terpenoids and other natural products including triglycerides may also be considered oils for purposes of the present invention.

In addition to the above-described oils, so called "silicone oils" such as polydimethylsiloxanes with viscosities ranging from about 0.5 cps to several million cps, polyphenylmethylsiloxanes, crosslinked polysiloxane elastomers, cyclomethicones and combinations of polydimethylsiloxanes with alkyl groups may be used. These "silicones may be used singly, in combination and in combination with other suitable cosmetic "oils".

Preferred oils for use in the present invention include petrolatum, mineral oil or mixtures of petrolatum and mineral oil where the amount of petrolatum to mineral oil (on a weight/weight basis) ranges from about 1:20 to about 10:1, preferably about 1:5 to about 5:1, more preferably about 1:3 to about 1:1, depending upon the end use of the emulsion composition. The inclusion of petrolatum and/or mineral oil and/or the ratio of petrolatum to mineral oil in the present compositions will greatly influence the final viscosity of the o/w compositions according to the present invention.

Emulsions according to the present invention comprise water in an amount ranging from about 25% to about 90%, about 35% to about 85%, about 40% to about 80%, about 45% to about 75% by weight and an oil (or combination of oils) in an amount ranging from about 5% to about 65%, about 10% to about 50%, about 15% to about 50%, with at least one surfactant being added to the emulsion in an amount ranging from about 0.1% to about 20% or more by weight, about 0.5% to about 15% by weight, about 0.75% to about 12.5% by weight, about 1% to about 10% by weight, about 0.5% to about 7.5% by weight, about 0.25% to about 5% by weight, with the character of the surfactant (cationic, anionic or neutral) influencing the amount of other components be added in the first emulsion as well as the second emulsion.

In addition to the above components which are included in each emulsion part of the present invention, additional components may be added to the emulsion (one or both of the two part composition so that the final surface film composition comprises the component) including fragrances, emollients, solvents/diluents, opacifiers, sunscreen agents, anti-perspirants, deodorizers, antiperspirants, preservatives, antimicrobial agents, dyes, pigments, foaming agents, gelling agents, solubilizing agents, humectants, stiffening agents and mixtures of these components, among numerous other components which may be added to personal care products (compositions). These are all added and included in effective amounts.

The following examples are provided to exemplify the present invention. They are to provide a further description of the present invention and are not to be taken to limit the invention in any way.

Examples are shown below:

EXAMPLES 1 & 2

| Ingredients | 1 % | 2 % |
| --- | --- | --- |
| Behenic Acid | 1.0 | — |
| Stearyl Alcohol | 1.5 | 1.5 |
| Cetyl Alcohol | 1.5 | 1.5 |
| Sodium Hydroxide (aq 50%) | 0.5 | — |
| Behentrimonium Methosulfate | — | 1.0 |
| Jojoba seed oil | 15.0 | 15.0 |
| Deionized Water | 79.5 | 80.0 |
| Fragrance, Color, Humectant, Preservative | QS | QS |
|  | 100.0 | 100.0 |

Both of these formulas exhibit good stability surviving 50° C. storage for at least one month, 5 freeze/thaw cycles and room temperature storage for over three years with no indications of separation, discoloration or changes in odor. When applied separately to the hands, Example 1 is a typical anionic emulsion exhibiting good rub in with a typical "break" as it dries and an oily residual feel because of the relatively high Jojoba oil level. Example 2 is similar in application feel, but without the noticeable break. The residual feel is also oily rather than the typical powdery feel that one expects from a quaternary emulsifier, again because of the relatively high oil level. When co-dispensed into the hand and mixed, the emulsifiers immediately react to form a high viscosity, waxy feeling emulsion that is noticeably different from either of the two component emulsions. When rubbed and distributed on the hands, this combination is much less oily feeling, but it does feel as if the oil has "plated out" on the skin and the water phase liquid is being rubbed on top of it. This is similar to the rub in feel of a polymeric emulsion. When combined in a beaker in equal weights, the result is an emulsion that is thicker than either of the component emulsions and shows increasing signs of graininess and clumping which are indicative of instability and eventual separation. After application of the combined lotions to the hands, they are noticeably "waterproofed" and readily shed water when rinsed under running tap water and the residual water "beads" in droplets on the skin.

Examples 3 and 4 illustrate the use of silicone "oils" rather than jojoba oil.

EXAMPLES 3 & 4

| Ingredients | 3 % | 4 % |
| --- | --- | --- |
| Behenic Acid | 1.0 | — |
| Stearyl Alcohol | 1.5 | 1.5 |
| Cetyl Alcohol | 1.5 | 1.5 |
| Sodium Hydroxide (aq 50%) | 0.5 | — |
| Behentrimonium Methosulfate | — | 1.0 |
| Cyclopentasiloxane | 10.0 | 10.0 |
| Dimethicone (200 cps) | 1.0 | 1.0 |
| Deionized Water | 84.5 | 85.0 |
| Fragrance, Color, Humectants, Preservative | QS | QS |
|  | 100.0 | 100.0 |

These Examples have similar stability to Examples 1 & 2, but their application feel is quite different. The main difference is that the individual emulsions are not as oily feeling after the products have dried on the skin and the rub-in is faster with both emulsions showing a more noticeable break. During application and rub-in of the co-dispensed products, the viscosity of the combined products increases noticeably. The combined product rubs-in quickly with a strong break in which the oily material again seems to plate out onto the skin leaving the water phase on top. The final combined product dries with a minimal oily feel and leaves the hands noticeably "waterproofed", readily shedding water when rinsed under running tap water and causing the residual water to "bead" in droplets on the skin.

Co-dispensing Example 1 with Example 4 or Example 2 with Example 3 gives an application feel that is intermediate between that observed with the Examples 1 and 2 or Examples 3 and 4 co-dispensed products. Again the viscosity of the combined co-dispensed products is noticeably higher than that of either emulsion alone.

EXAMPLES 5, 6, 7 & 8

| Ingredients | 5 % | 6 % | 7 % | 8 % |
| --- | --- | --- | --- | --- |
| Stearic Acid | 1.0 | — | — | — |
| Stearyl Alcohol | 1.5 | 1.5 | 1.5 | 1.5 |
| Cetyl Alcohol | 1.5 | 1.5 | 1.5 | 1.5 |
| Quaternium 18 | — | 1.0 | — | — |
| Polylipid B[1] | — | — | — | 1.0 |
| Dicaprylyl Maleate | 5.0 | 10.0 | — | 10.0 |
| NuLastic Silk D-99-6[1] | — | — | 20.0 | — |
| Ethylhexyl Methoxycinnamate | 5.0 | — | — | — |
| Benzophenone-3 | 5.0 | — | — | — |
| Z-Cote HP-1[2] | — | 5.0 | — | — |
| Pemulen TR-1[3] | — | — | 0.2 | — |
| Triethanolamine | 0.5 | — | 0.2 | — |
| Deionized Water | 80.5 | 81.0 | 76.6 | 86.0 |
| Fragrance, Color, Humectant, Preservative | QS | QS | QS | QS |
| | 100.0 | 100.0 | 100.0 | 100.0 |

These Examples illustrate other aspects of the invention and allow different combinations of anionic and cationic emulsifiers to produce different end results. Example 5 is an anionic emulsion that contains two typical sunscreens that are organic UV absorbing compounds.

Example 6 is a cationic emulsion that uses Zinc Oxide as a physical sunscreen. It is desirable to make cationic emulsions with Zinc Oxide because of the slight release of Zinc ions which can react with anionic emulsifiers making them insoluble which, in turn, can make the emulsion unstable. Combining these two Examples upon application to the skin allows the combination of the sunscreens, and optimizes the stability of the sunscreen ingredients and the emulsions. Mixing the two formulas also improves the water wash-off resistance of the combined product by reducing the water solubility of the two primary surfactants.

Example 7 describes an anionic emulsion that is formed through the use of an anionic polymer with pendant alkyl groups that functions as both an emulsifier and a viscosity building agent. Example 8 is another cationic emulsion based upon a quaternized ammonium polyurethane with pendant behenyl alkyl groups that functions as both an emulsifier and a viscosity building agent. Combining these two Examples upon application produces an immediate reaction between the oppositely charged polymeric emulsifiers that precipitate and produce a film that is very resistant to water wash-off.

As described previously, Example 5 can be combined with Example 8 to produce a final product with a lower amount of sunscreen agents, but with a less oily rub-in feel, but still having significant resistance to water wash-off. Similarly, combining Example 6 with Example 7 gives a final product that has the aesthetic feel of a silicone elastomer product and provides resistant to water wash-off and UV protection.

EXAMPLES 9 & 10

| Ingredients | 9 % | 10 % |
| --- | --- | --- |
| Deionized Water | 74.7 | 75.7 |
| Glycerin | 3.0 | 2.0 |
| Pemulen TR-1 | 0.2 | — |
| Triethanolamine | 1.0 | — |
| Stearic Acid | 1.0 | — |
| Glyceryl Monostearate | 4.0 | — |
| NuLastic Surfa D-99-9[1] | 15.0 | 15.0 |
| Quaternium 70 (and) Propylene Glycol | — | 2.0 |
| Cetearyl Alcohol | — | 4.0 |
| Polyderm PPI-SA[1] | — | 0.2 |
| Fragrance, Color, Humectants, Preservative | QS | QS |
| | 100.0 | 100.0 |

These examples, when combined, produce an elegant non-oily feeling film on the skin that resists water wash off and causes the water to bead on the skin.

The following examples illustrate the use of oppositely charged polymers in separate emulsion formulas to enhance the feel and water wash off resistance of the combined products.

EXAMPLES 11 & 12

| Ingredients | 11 % | 12 % |
| --- | --- | --- |
| Deionized Water | 79.5 | 79.5 |
| Glycerin | 3.0 | 3.0 |
| Crodafos CES (Ceteryl Alcohol (and) | 6.0 | — |
| Dicetyl Phosphate (and) Ceteth-10 Phosphate | — | — |
| Cetearyl Alcohol | — | 4.0 |
| Isohexyl Caprate | 10.0 | 10.0 |
| Sodium Polyacrylate | 0.5 | — |
| Polyderm PPI-SA[1] | — | 1.0 |
| Polyderm PPI-SA15 | — | 1.0 |
| Merquat 100 | — | 0.5 |
| Fragrance, Color, Humectants, Preservative | QS | QS |
| pH adjusters | 100.0 | 100.0 |

These examples, when combined, produce a soft combined emulsion that dries to a slightly waxy, non oily feeling film that becomes slippery and oily feeling when wetted, yet resists wash-off and causes water to bead on the skin. These types of formulas that combine anionic polymers with an anionic surfactant emulsion formula and cationic polymers with a cationic emulsion formula will greatly enhance the overall film forming properties when the emulsions are combined. The precipitation of anionic and cationic polymer when combined is a well known phenomenon and usually results in the formation of a water insoluble, intractable, unaesthetic mass. By making two separate emulsions, the polymers are kept in combination with compatible surfactants and oils that help to solubilize them and keep them dispersed when the two emulsions are combined and mixed together on the skin. Thus, the precipitation is controlled resulting in a smoothly applied film that protects the skin and will help desired materials such as humectants, sunscreens and pharmaceutically active ingredients to deposit and remain on the skin.

EXAMPLES 13 & 14

| Ingredients | 13 % | 14 % |
| --- | --- | --- |
| Deionized Water | 72.5 | 82.5 |
| Glycerin | 1.0 | 1.0 |
| Crodafos CES (Ceteryl Alcohol (and) Dicetyl Phosphate (and) Ceteth-10 Phosphate | 6.0 | — |
| Cetearyl Alcohol (and) Behentrimonium Methosulfate | — | 6.0 |
| Isononyl Isononanoate | 10.0 | 10.0 |
| Sodium Polyacrylate | 0.5 | — |
| Benzophenone-4 | 10.0 | — |
| Merquat 100 | — | 0.5 |
| Fragrance, Color, Humectants, Preservative | QS | QS |
| pH adjusters | 100.0 | 100.0 |

These examples, when combined, produce a composition that dries to a non oily feeling film that becomes somewhat slippery feeling when wetted, yet resists wash-off and causes water to bead on the skin. The Benzophenone-4 is a water soluble UV absorber that is approved for use in sunscreen formulations, however it is not widely used even though it is an effective UVA/UVB absorber because of its water solubility. This formula can be used to insolubilize the Benzophenone-4 on the skin and prolong its activity because the Benzophenone-4 complexes with the Behentrimonium Methosulfate and the Merquat 100 to form an ionic complex that is much less water soluble.

The present invention has been described in detail hereinabove, by way of a description of the invention as well as the presentation of non-limiting examples. The following non-limiting claims set forth the present invention.

What is claimed:

1. A method of applying a water wash-off resistant, aesthetically pleasing, two part emulsion product comprising combining two emulsion products at the point of application on a surface, wherein one of the emulsions comprises an effective amount of an anionic emulsifier and the other emulsion comprises an effective amount of a cationic emulsifier, wherein at least about 50% by weight of the emulsifiers react and precipitate out of the emulsions when the two parts are mixed and applied to an application surface, leaving behind a water-resistant film surface composition.

2. The method of claim 1 wherein said anionic emulsifier is a fatty acid soap, an alkyl sulfate, an alkyl phosphate or a polymeric anionic emulsifier.

3. The method of claim 1, wherein said cationic emulsifier is a mono fatty quaternary ammonium salt, a di fatty quaternary ammonium salt, a tri fatty quaternary ammonium salt or a polymeric cationic emulsifier.

4. The method of claim 1, wherein the cationic emulsifier is a mono fatty ammonium salt, a di fatty ammonium salt, a tri fatty quaternary ammonium salt or a polymeric fatty alkyl ammonium salt.

5. The method of claim 1, wherein the anionic emulsion and the cationic emulsion are co-dispensed from a single package with separate dual chambers onto said application surface.

6. The method of claim 5, wherein the two emulsions are dispensed onto a keratinous surface and subsequently mixed by hand.

7. The method of claim 5, wherein the two emulsions are combined as they are dispensed from their separate chambers by forcing them through a static mixer or Combining them in a mixing chamber prior to being dispensed onto a keratinous surface.

8. The method according to claim 1 wherein one or both of the emulsions contain sunscreen agents.

9. The method according to claim 1 wherein one or both of the emulsions contain pharmaceutical active ingredients.

10. The method according to claim 1 wherein one or both of the emulsions contain pigments.

11. The method according to claim 1 wherein one or both of the emulsions contain light diffusing materials.

12. The method according to claim 1 wherein one or both of the emulsions contain colorants.

13. The method according to claim 1 wherein one or both of the emulsions contain at least one component selected from the group consisting of preservatives, antioxidants, chelating agents, fragrances and UV colorant protectants.

14. The method according to claim 1 wherein one or both of the emulsions contain humectants.

15. The method according to claim 1 wherein one or both of the emulsions contain polishing agent.

16. The method according to claim 1 wherein one or both, of the emulsions contain shining agents.

17. The method according to claim 6 wherein said keratinous surface is skin.

18. The method according to claim 6 wherein said keratinous surface is hair.

19. The method according to claim 6 wherein said keratinous surface is ungual tissue (nails).

20. The method according to claim 15 wherein said polishing agents are selected from the group consisting of silicas, clays, rouges and mixtures thereof.

21. The method according to claim 16 wherein said shining agents are selected from the group consisting of dimethylpolysiloxanes.

22. The method according to claim 1 wherein said emulsion comprising said anionic emulsifier further comprises an anionic polymer.

23. The method according to claim 1 wherein said emulsion comprising said cationic emulsifier further comprises a cationic polymer.

* * * * *